(12) United States Patent
Ellison

(10) Patent No.: US 8,003,946 B2
(45) Date of Patent: Aug. 23, 2011

(54) METHOD FOR DETECTING LOCALIZED DEFECTS PRESENT IN A MINERAL FIBER MAT

(75) Inventor: Christopher Ellison, Liancourt (FR)

(73) Assignee: Saint-Gobain Isover, Courbevoie (FR)

( * ) Notice: Subject to any disclaimer, the term of this patent is extended or adjusted under 35 U.S.C. 154(b) by 311 days.

(21) Appl. No.: 12/299,912

(22) PCT Filed: May 9, 2007

(86) PCT No.: PCT/FR2007/051240
§ 371 (c)(1),
(2), (4) Date: Nov. 7, 2008

(87) PCT Pub. No.: WO2007/128942
PCT Pub. Date: Nov. 15, 2007

(65) Prior Publication Data
US 2009/0179152 A1    Jul. 16, 2009

(30) Foreign Application Priority Data
May 10, 2006 (FR) ..................... 06 51683

(51) Int. Cl.
*G01F 23/00* (2006.01)
*G01R 23/20* (2006.01)

(52) U.S. Cl. .................... 250/358.1; 324/639
(58) Field of Classification Search ............ 250/358.1, 250/306, 372, 559.27; 427/8, 389.8, 9; 700/122; 324/637, 638, 639
See application file for complete search history.

(56) References Cited

U.S. PATENT DOCUMENTS

| | | | |
|---|---|---|---|
| 4,203,155 | A | 5/1980 | Garst |
| 5,625,293 | A | 4/1997 | Marrelli et al. |
| 2006/0019024 | A1 | 1/2006 | Freeman et al. |

FOREIGN PATENT DOCUMENTS

| | | |
|---|---|---|
| DE | 100 53 112 | 5/2002 |
| GB | 2 300 483 | 11/1996 |
| WO | 2006 023137 | 3/2006 |

*Primary Examiner* — David Porta
*Assistant Examiner* — Faye Boosalis
(74) *Attorney, Agent, or Firm* — Oblon, Spivak, McClelland, Maier & Neustadt, L.L.P.

(57) ABSTRACT

The invention concerns a method for detecting localized defects, such as hot spots or wet spots, present in a mat of mineral fibers bonded by a binder, including using a microwave radiation of frequency ranging between 1 and 50 GHz, preferably between 5 and 10 GHz, the total power of the emitted electromagnetic wave ranging between 0.1 and 5 watts, preferably of the order of 1 watt. The invention also concerns a device for implementing said method as well as an installation for continuously making mineral fiber mats containing said device.

17 Claims, 2 Drawing Sheets

METHOD FOR DETECTING LOCALIZED DEFECTS PRESENT IN A MINERAL FIBER MAT

CROSS-REFERENCE TO RELATED APPLICATIONS

This application is a 371 of PCT/FR07/51240 filed May 9, 2007 and claims the benefit of FR 0651683 filed May 10, 2006.

The invention relates to the field of materials consisting of a mineral fiber mat, in particular rock fibers or glass fibers. More particularly, the present invention relates to the detection of localized faults that may be present within fiber mats, in particular in or coming from a manufacturing process of products designed for acoustic and/or thermal insulation, or even used as a growth support or substrate for plants.

The insulation materials currently on the market consist of a mat or felt made of mineral fibers, such as glass fibers or rock fibers bound by an organic binder.

The manufacturing process for these fiber mats is well known and typically comprises, for example in the case of a rock wool panel, the following steps in succession:
- melting of the rock, generally in a cupola furnace at a temperature of around 1500° C.;
- fiberization, i.e. obtaining rock fiber by introducing molten material into an external centrifugation device known for this purpose and most often called a spinner, for example as described in the patent EP 119 124;
- spray coating of a sizing compound comprising a generally thermosetting binder in aqueous solution onto the newly formed fibers;
- collection of the fibers impregnated with the binder in a collection chamber comprising, opposite the fiberization device, a conveyor equipped in its lower part with suction boxes kept at low pressure;
- curing in a stove or an oven at a temperature and for a sufficient duration to allow hardening and crosslinking of the binder and the elimination of residual water;
- longitudinal cutting of irregular edges, and optionally of the center, of the lengthwise continuous fiber mat thus obtained by means of saws positioned along the conveyor;
- cutting of the mat in a transverse direction and optionally in the thickness direction (slitting) so as to obtain blocks that can then be either arranged in boards or in rolls, generally by means of a saw or a guillotine; and
- storing of the boards or rolls on a pallet before dispatch.

The glass wool manufacturing process is broken down in a similar manner except that a furnace is used for the melting and an internal centrifugation device for the fiberization, for example as described in EP 91866.

In the context of monitoring the manufacturing process such as just described, it is necessary to continuously carry out monitoring procedures over at least part and preferably over the whole of the production in order to guarantee good quality of the mat. Such monitoring relates in particular to the degree of curing of the binder on leaving the oven, via measurement of the residual water content of the fiber mat and/or estimation of the degree of polymerization of the binder, for example.

It is quite obvious that these monitoring procedures must not, however, disturb the proper running of the various steps of the process. In particular, according to certain essential features sought, such procedures must be able to be implemented efficiently and easily on a preexisting production line, without entailing significant additional costs. According to another important parameter, the monitoring of the process must be reactive, i.e. the measurement must be able to be carried out in a time sufficiently short to allow rapid action by the operator and hence avoid scrapping and the loss of part of the production, or at least to limit the loss undergone to the minimum.

The method should preferably be noninvasive in type, that is to say that it does not require the incorporation of foreign elements into the fiber mat. Known invasive methods are, for example, the methods involving the use of a temperature measurement by thermocouples loaded in the product, where necessary with a recording device, as for example described in the application WO 2006/017106. Also known are methods involving the use of chemical reagents such as a pH indicator. In general, such methods are manual and require a sample to be taken on the line and subsequently analyzed in the laboratory.

According to another route, the patent application WO 2006/023137 describes, for example, a method of monitoring the process based on a measurement by spectroscopic means of the residual moisture present in the fiber mat impregnated with binder, before the heat treatment crosslinking the binder in the stove.

More precisely, the method comprises a measurement of the overall residual moisture content, i.e. the overall quantity of water present in the mat on leaving the fiber collection chamber. By comparing said residual moisture content with a reference value, the adjustment of at least one parameter allows continuous monitoring of the process. According to this document, this parameter may be chosen from among the quantity of water initially mixed with the binder, the temperature of the collection box or the level of vacuum applied at the suction boxes.

With the usual phenol-formaldehyde resins that become yellow with curing, this monitoring may be done visually through assessment of the color of the product by an operator. This method is nonetheless approximate with regard, in particular, to more localized defects and in addition it does not enable defects within the thickness of the product to be detected.

It is to be noted that the importance and the necessity of an efficient monitoring method in the manufacturing processes of mineral fiber mats are currently being reinforced due to the desire to develop alternative binder systems as a replacement for phenol-formaldehyde resins, which would allow the risks of formaldehyde emission during curing of the binder to be reduced.

More particularly, binders of a different chemical nature are currently being studied, in particular obtained from polycarboxylic polymers and from polyols such as the acrylic resins, for example as described in the application WO 2006/023137. In contrast to phenol-formaldehyde resins, these binders do not exhibit changes in appearance or color which are characteristic of curing. Moreover, in order to avoid excessive premature curing setting and of such binders and to reduce the viscosity thereof, it is necessary to increase appreciably, relative to phenol-formaldehyde resins, the proportion of water present in the solution sprayed onto the newly formed fibers, which leads to increased difficulties in eliminating the residual water potentially present in the finished product on leaving the line, and hence makes the presence of tools continuously monitoring the production, responding if possible to all the previously described characteristics, even more indispensable.

However, at the current time there exist only very few systems meeting all these requirements and continuously monitoring the quality of the fiber mat efficiently, whether this is on leaving the line or at a later stage, i.e. after the production itself.

Among several known methods, those including devices generating radiation may be cited, such as gamma probes or gamma gauges such as those described in the patent EP 118369 or X-rays, but such equipment, apart from being relatively expensive, requires extremely stringent safety measures to be taken for the safety of personnel, notably with the need to provide a large safety perimeter around the source.

Other known methods are, for example, spectroscopic methods based on infrared (IR) radiation to measure the overall residual moisture content of the fiber mat. However, as the penetrating power of IR is relatively low, the analysis is limited to the outermost part of the mat and the moisture content at the center of the material, which may be relatively large, cannot be determined by this method.

Moreover, all noninvasive methods currently used or known for monitoring the quality and the homogeneity of a mineral fiber mat bound by a binder only take account of an average value at a time t, within a portion of the material, of the control parameter, in particular of the overall water content present within said portion.

In particular, such methods are not discriminating enough to distinguish localized defects, i.e. defects present only at certain very localized points of the felt. These defects can be classed in two main categories:

1st) "wet" defects or wet spots, which correspond to very localized sites on the felt. These defects appear in particular in places where a build-up of higher fiber density, water and resin (binder) forms during the fiberization step. During the step of drying by suction, the hot air passing across the mat then tends to go round this higher density point, at which a higher concentration of resin therefore remains. Such wet spots lead to a gradual emission of formaldehyde until a very long time after manufacture. Of course, such emissions must be only exceptional, or even nonexistent, in the finished product, in particular with regard to the current or future tightening up of standards.

Furthermore, wet spots are very detrimental to certain particular uses of fiber mats and in some extreme cases prevent these uses. For example, the presence of such defects in a fiber mat used as a growth support or substrate for plants causes plants positioned near them to die.

Finally, in many applications, annealing of the entire production, which is very expensive, proves necessary to be certain of the absence of such wet spots.

2nd) defects of the "hot spot" type, which correspond to areas with high rock or glass density. Such defects result from the fiberization process and appear in particular due to instabilities or to accumulation of shot. They are characterized by very localized build-ups inside the fiber mat. These build-ups may either cool within the felt and hence give rise to extremely dense and tough areas on which the cutting devices (saw, guillotine) may then break or crack, or continue to fuse slowly, which may in extreme cases lead to the entire product catching fire, for example in storage areas.

Of course, what has just been described constitutes only a few examples of localized defects in the sense of the present invention, which is obviously not limited to the detection of these defects alone. Generally speaking, any defect contributing to a local variation such as a local increase (or decrease) in the concentration of fibers and/or water and/or binder within the mat must be considered to be included in the present invention. In particular, the detection of a defect constituted by a local increase in the density or weight of the fiber mat is included in the scope of the present invention.

More particularly, the present invention relates to a method allowing all the abovementioned problems to be solved, in particular enabling the detection of localized defects, for example but not limited to, those of the hot spot or wet spot type, present in a mineral fiber mat bound by a binder, comprising the use of microwave radiation with a frequency between 1 and 50 GHz, preferably between 5 and 10 GHz, the total power of the electromagnetic wave emitted being between 0.1 and 5 watts, preferably around or less than 1 watt, or even around or less than 0.5 watts.

Surprisingly and unexpectedly, the experiments carried out by the applicant, of which several examples will be provided in the subsequent description, have shown that such low powers were nevertheless sufficient to analyze the entire thickness of a fiber mat. By way of example, it was possible to visualize, according to the present method, the presence of the previously described localized defects in felts, the thickness of which is between 30 and 400 mm or even greater and the density of which is between 6 and 220 $kg/m^3$ or even higher. Typically, the density of glass wool may, for example, be between 6 and 140 $kg/m^3$ and the density of rock wool may be between 20 and 220 $kg/m^3$.

It is of course possible, according to the invention, to vary the power of the incident microwaves according to one or another of these parameters. However, according to one of the essential aspects of the invention, this power always remains within values of the order of the watt. Their employment, in contrast to the majority of noninvasive monitoring methods currently used, therefore presents no hazard to personnel. In particular, the present method does not require precautions for use for the safety of the personnel, nor the need to provide a large safety perimeter around the measurement device, in particular in the sense of the Directive 2004/40/CE of the European Parliament pertaining to the minimum regulations for the exposure of workers to electromagnetic fields. By way of comparison, it has been possible to measure that the power emitted around the antenna of a mobile telephone is around 2 watts.

For example, the presence of said defects is characterized by a measurement of the phase shift of microwave radiation and/or modification of the amplitude of said radiation, when this radiation passes through the mineral fiber mat.

According to a preferred embodiment, the incident microwave radiation is employed by means of a series or an array of microwave emitter devices, positioned approximately transversely facing one side of the mat and oriented in the direction of said mat. After passing through said mat, the signal is collected by a series or an array of receiver probes or sensors positioned approximately transversely facing the opposite side of the mat. The sensor array is preferably placed in line with the transmitter array.

Advantageously, the fiber mat passes between the array of transmitter devices and the array of receiver probes, the detection of said defects being carried out continuously over the entire width of the fiber mat.

Typically, the fiber mat passes along a roller conveyor, the transmitter devices and the sensors being positioned above and below the conveyor respectively.

The gap between the sensors may be chosen depending on the size of said defects, the gap between the sensors being for example between 1 and 100 mm, preferably between 5 and 20 mm.

The invention furthermore relates to a device allowing the implementation of the detection method previously described, comprising means for generating microwave radiation with a frequency of between 1 and 50 GHz, preferably between 5 and 10 GHz, the total power of the electromagnetic wave emitted being between 0.1 and 5 watts, preferably around or less than 1 watt, and means for detecting the electromagnetic wave after passing through the fiber mat.

The generation means include, for example, a series or an array of microwave transmitter devices positioned so as to be able to be oriented transversely along one side of the mat and in the direction of said mat. The detection means comprise, for example, a series or an array of sensors positioned transversely facing the opposite side of the fiber mat. The generation means are preferably placed in line with the detection means.

According to a preferred embodiment, the device furthermore comprises means for processing and displaying the signal.

The invention also relates to an installation for manufacturing a continuous mineral fiber mat bound by a binder, of the rock wool or glass wool type, comprising means for fiberizing the mineral fibers, means for synthesizing and spraying the binder, and means for collecting, conveying and crosslinking the fibers, said installation furthermore comprising a detection device as described above, positioned at the outlet of the crosslinking means.

Advantageously, the detection device is then either coupled to means for regulating at least one parameter chosen from the group consisting of the composition of the binder, the suction force, the crosslinking temperature of the fibers, the residence time in the crosslinking means, or coupled to means for regulating a piece of equipment positioned downstream of the microwave analysis device, said piece of equipment being configured to isolate and/or downgrade the areas of the mat that include the defects or to mark said areas, very precisely for example with a view to subsequent sorting or cutting.

The details of the invention will be better understood on reading the following description of an implementation of the present device within a line for fiberizing a mineral wool mat. Within the scope of the present invention other embodiments are of course possible, the following description being provided solely by way of illustration and not to be considered as limiting in any of the aspects described.

Figure 1:
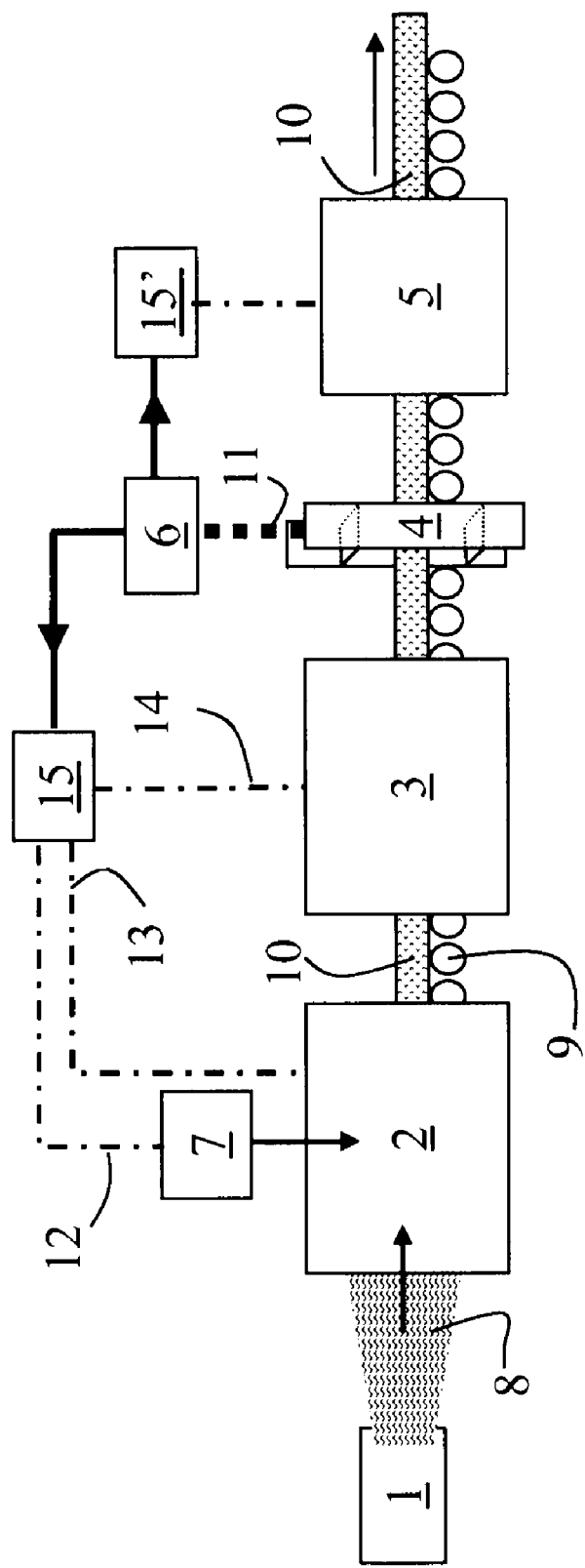
FIG. 1 represents an overview of a manufacturing scheme for mineral wool incorporating the present invention.

FIG. 1 represents schematically a fiberization installation such as previously described. The installation comprises a device 1 of known technology, enabling the fiberization of the rock or of the glass. According to a well-known process, the fibers 8 are collected in the form of a mat in a collection chamber 2 such as already described at the same time as a sizing compound is spray coated onto the newly formed fibers 8 by dedicated means 7 for mixing and injecting the various constituents (resin, water, additives etc.).

Figure 2:
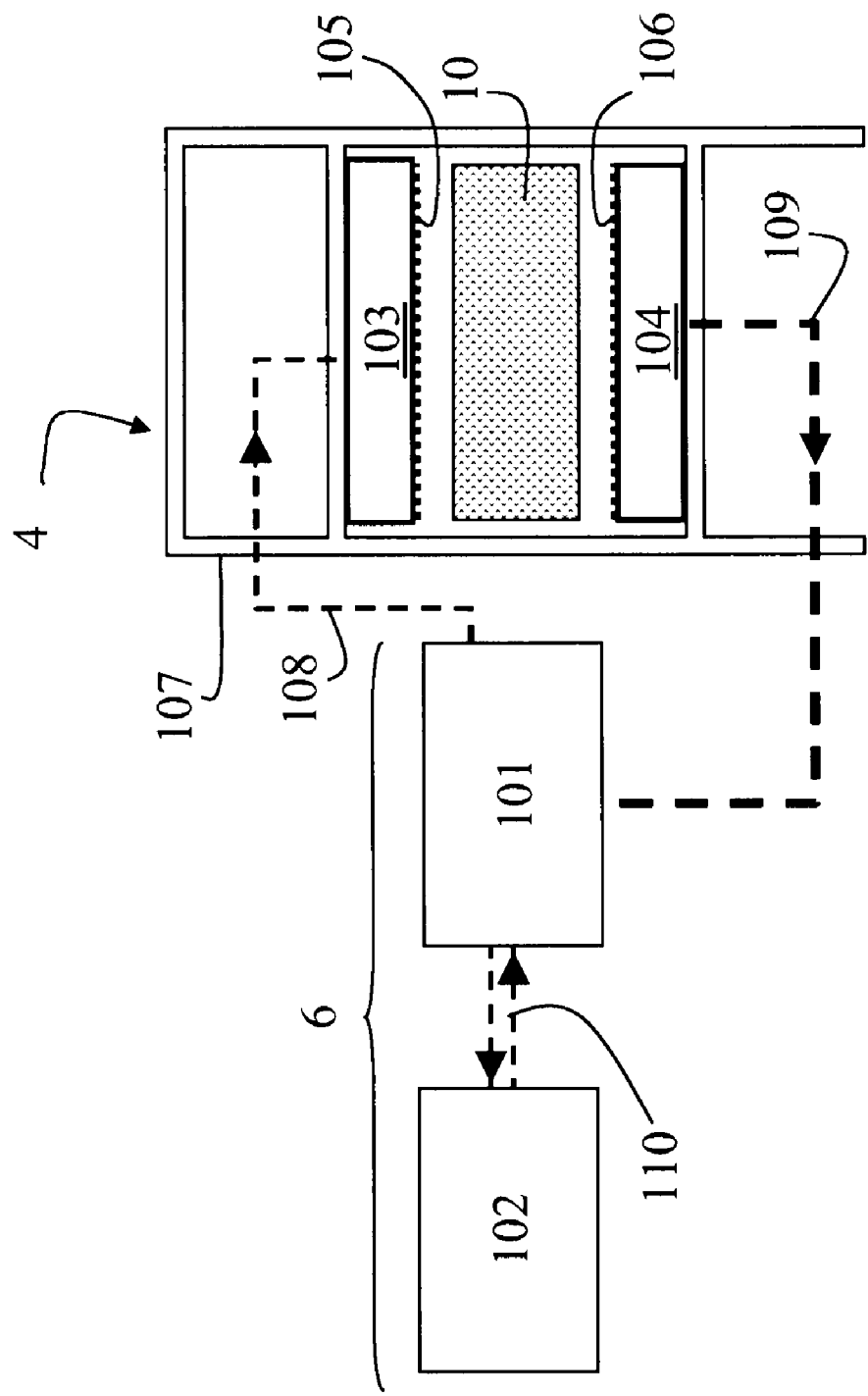
FIG. 2 is a more detailed schematic view of an exemplary embodiment of the device according to the invention.

The fiber mat 10 is then calibrated and sent by conveyor means 9 into an oven 3, the temperature of which is, for example, close to 400° C. The rise in temperature and the residence time of the fiber mat in the oven are adjusted to allow curing of the binder and the elimination of the water. On leaving the oven 3, the continuous fiber mat then undergoes continuous monitoring by the low-power microwave device according to the invention. The device 4 then detects according to the invention possible localized defects present over the entire length and the entire thickness of the fiber mat. The collected information 11 is transmitted to a device 6 for processing and amplifying of the output signal and optionally displaying it. An embodiment and the mode of operation of the device 6 are illustrated by FIG. 2.

After processing by the device 6, if the signal 11 indicates the presence of localized defects, the information is transmitted to a monitoring device 15 which is then able to modify continuously and within a very brief delay at least one of the parameters affecting a step of the manufacturing process, for example via the control lines 12, 13, 14. Said parameter may for example, but not limitingly, be the quantity of binder injected, the initial composition of the mixture and in particular the quantity of water present with the resin (control line 12), the temperature of the oven (line 14), the suction force of the boxes (line 13) etc.

According to another possible embodiment of the invention, which may be coupled with the preceding one, a monitoring device 15' manages a piece of equipment 5 positioned downstream of the microwave analysis device 4. This piece of equipment may have the role, for example, of isolating and/or downgrading the areas of the mat that include the defects or marking said areas very precisely, for example with a view to subsequent cutting or sorting. Such an embodiment also allows on the one hand a constant production quality to be ensured and on the other hand the fraction of the production that has to be wasted or recycled to be restricted to an absolute minimum. Of course, other embodiments and variations of the process for monitoring the manufacture are possible and must be included within the scope of the present invention.

In particular, the device according to the invention may also be used for monitoring the quality of the mineral wool and its sorting for any "off-line" application. For example, it is possible, without departing from the scope of the invention, for a finer sorting to be carried out, in the factory or possibly at a customer's premises depending on the latter's needs, in a cutting shop or finishing plant using the present device. This allows in particular defects to be avoided and to guarantee that defects, usually acceptable for an ordinary application, do not enter into the composition of the fiber mat, when a more specific application is envisioned (for example, but not limitingly, plant cultivation).

FIG. 2 schematically represents the operation of the detection device 4 and the signal generation/processing device 6. In FIG. 2 the device 6 comprises a unit 101 for generating, receiving and amplifying radiofrequency RF signals of known technology and a unit 102 for processing and displaying the signal, including an interface 110 with a microcomputer on which the defects present over the entire width and in the entire thickness of the mat 10 may be displayed. The passing of the mat through the detection device 4 and the immediate processing of the signal obtained by the device 6 advantageously allow the defects present over the entire length of the mat to be characterized almost in real time on the line. The RF unit 101 generates a suitable radiofrequency signal which supplies an antenna 103 via a radiofrequency cable 108. In a known manner, the incident signal is, for example, split by a series of dividers, such that a microwave signal or radiation having a uniform wavefront and a wavelength approximately equal to the width of the mat is generated, at the antenna 103, in the direction of the mat 10 by a series of transmitters 105. These transmitters are, for example, positioned transversely, for example in N arrays of n areas or patches regularly spaced, for example by 10 mm, at the level of the lower part of the antenna. The method consists in a measurement over the entire width of the fiber mat of the transmission coefficient through this mat. It would not, however, depart from the scope of the invention, if the measurement were carried out on reflection, after the incident microwave radiation has passed through the fiber mat.

According to the invention, the total power generated by all the transmitters 105 is of the order of the watt, or even less.

The radiation, after passing through the mat 10, is collected, at the receiver part 104, by at least an array of sensors 106 positioned transversely facing the opposite side of the mat 10. The collector part typically comprises a "retina" consisting of a suitable number of probes incorporating active elements, divided for example into N arrays of n areas or patches, within a collector antenna. The number of probes used and the spacing between two successive probes depends on the width of the mat to be studied and on the desired resolution, in particular with regard to the size of the defects being sought. According to the principle of the invention, the presence of a localized defect according to the invention within the fiber mat, through which the low-power incident microwave wave passes, causes electromagnetic interference of the latter and a modulation of the signal. On leaving the receiver part 104, the modulated microwave signal, the amplitude and phase of which depend on the nature and the size of the defects encountered by the radiation, is collected.

The modulated signal is then transmitted and processed according to known techniques, for example such as described in the following, by the units 101 and 102 via a radiofrequency cable 109. The microwave transmitter and receiver parts are positioned on a stand 107, itself arranged around the roller conveyor device 9, such as indicated in FIG. 1.

Examples of microwave technology operating according to the previously described principles and capable of being used according to the invention are described in particular in the scientific publications "Materials Research Society Symposia Proceedings, year 1991, volume 189, pages 49-53" or "International Microwave Symposium Digest, year 1990, volume 3, pages 1133-1136", to which reference should be made for details of the implementation.

According to the invention, the detection and the processing of the signal may be carried out according to all the signal analysis and processing techniques known to the art, for example by thresholding, by geometric and/or arithmetic averaging, or by the use of other signal processing and filtering algorithms, and by fringe analysis of the diffraction between signals, in particular in order to amplify the detection. According to an advantageous possibility for implementing the invention, the algorithms use amplitude and phase deviations as operators allowing filters to be constructed and the presence or the absence of defects to be confirmed.

The following examples, provided with a solely illustrative aim, illustrate the advantages of the present invention:

EXAMPLES

Various defects were observed or simulated on a rock wool mat on leaving a production line. For various thicknesses and densities of the fiber mat, the defects were characterized by using the device such as previously described in relation to FIG. 2. Observation is spoken of when the defects result directly from the fiberization process, and simulation is spoken of when the defects are intentionally introduced in the thickness of the rock wool mat, after fiberization and before the mat passes below the detection device.

The device was installed on a system for manufacturing panels of rock wool in the configuration described in FIG. 1.

The frequency of the microwave signal was fixed in all the examples at 9.4 MHz, the total power radiated by the transmitters 105 being 0.3 watts. The distance between two transmitters or sensors 105 is 10 mm. The distance between two receivers or sensors 106 is also 10 mm. In the simplest manner, the computer processing of the signal comprises a comparison of the maximum variation in the measurement provided by a phase and amplitude probe on passing the defect with a mean value obtained on a defect-free sample, or alternatively with a mean of measurements obtained for said probe while the fiber blanket passes. The maximum values of phase and amplitude deviations for each defect are listed, as absolute values, in table 1.

When a defect is observed by the device according to the invention, the part of the mat containing the defect was removed and analyzed. In all cases the analysis effectively revealed the presence of a defect in the thickness of the mat at the exact locations detected by the device, whether this is simply observed, i.e. comes from the fiberization process itself, or simulated, i.e. intentionally introduced after fiberization.

All the data is reported in table 1.

| Characteristics of the rock wool mat | Nature of the defect | Origin of the defect | Phase variation | Amplitude variation |
|---|---|---|---|---|
| Thickness 30 mm Density 110 kg/m³ | Wet point | observed | 80° | 70 to 80% |
| | Wet point | simulated (injection with a needle of 5 ml of water at the center of the mat) | 40° | 30% |
| | Hot point | observed (molten rock) | 60° | 60% |
| | Glass fragment | simulated (addition of molten 1 cm piece of glass to the mat) | 20° | 25% |
| | Residues coming from the furnace wall | simulated (piece of 3 cm diameter incorporated in the mat) | 30° | 30% |
| Thickness 100 mm Density 100 kg/m³ | Wet point | observed | 40° | 50% |
| Thickness 100 mm Density 40 kg/m³ | Density variation | simulated (local increase to 50 kg/m³) | 10 to 15° | 10% |
| | Residues coming from the furnace wall | simulated (pieces of refractory of 6 cm diameter) | 30° | 50% |

The invention claimed is:

1. A method for detecting localized defects present in a mineral fiber mat bound by a binder, comprising the use of microwave radiation with a frequency between 1 and 50 GHz, the total power of the electromagnetic wave emitted being between 0.1 and 5 watts, wherein said microwave radiation is collected and analyzed after having passed through said mineral fiber mat, and wherein the presence of said defects is characterized by a measurement of the phase shift of microwave radiation and/or modification of the amplitude of said radiation, when this radiation passes through the mineral fiber mat.

2. The method as claimed in claim 1, wherein the incident microwave radiation is employed by means of a series or an array of microwave emitter devices, positioned transversely facing one side of the mat and oriented in the direction of said mat, and wherein, after passing through said mat, the signal is collected by a series or an array of receiver probes or sensors positioned transversely facing the opposite side of the mat.

3. The method as claimed in claim 2, wherein the fiber mat passes between the array of transmitter devices and the array of receiver probes, the detection of said defects being carried out continuously over the entire width of the fiber mat.

4. The method as claimed in claim 3, wherein the fiber mat passes on a roller conveyor, the transmitter devices and the sensors being positioned above and below the conveyor respectively.

5. The method as claimed in claim 1, wherein the gap between the sensors is chosen depending on the size of said defects.

6. The method as claimed in claim 1, wherein the gap between the sensors is between 1 and 100 mm.

7. The method as claimed in claim 1, wherein the thickness of the mineral fiber mat is between 30 and 400 mm and wherein the density of the mineral fiber mat is between 6 and 220 kg/m$^3$.

8. A device for implementing the detection method described in claim 1, comprising means for generating microwave radiation with a frequency of between 1 and 50 GHz, the total power of the electromagnetic wave emitted being between 0.1 and 5 watts, and means for detecting the modulated electromagnetic wave after passing through the fiber mat.

9. The device as claimed in claim 8, wherein the generation means include a series or an array of microwave transmitter devices positioned so as to be able to be oriented transversely along one side of the mat and in the direction of said mat, and wherein the detection means comprise a series or an array of sensors positioned transversely facing the opposite side of the fiber mat.

10. The device as claimed in claim 8 further comprising means for processing and displaying the signal.

11. An installation for the manufacture of a continuous mineral fiber mat of the rock wool or glass wool type bound by a binder, comprising means for fiberizing the mineral fibers, means for synthesizing and spraying the binder, and means for collecting, means for conveying and means for crosslinking the binder, said installation further comprising a detection device as claimed in claim 8, positioned at the outlet of the crosslinking means.

12. The installation as claimed in claim 11, wherein the detection device is coupled to means for regulating at least one parameter chosen from the group consisting of the composition of the binder, the suction force, the crosslinking temperature of the fibers, and the residence time in the crosslinking means.

13. The installation as claimed in claim 11, wherein the detection device is coupled to means for regulating a piece of equipment positioned downstream of the microwave analysis device, said piece of equipment being configured to isolate and/or downgrade the areas of the mat that include the defects or to mark said areas, with a view to subsequent sorting or cutting.

14. The method as claimed in claim 1, wherein the localized defect is a hot spot or wet spot.

15. The method as claimed in claim 1, wherein the microwave radiation frequency is between 5 and 10 GHz.

16. The method as claimed in claim 1, wherein the total power of the electromagnetic wave emitted is around 1 watt.

17. The method as claimed in claim 1, wherein the gap between the sensors is between 5 and 20 mm.

* * * * *